(12) United States Patent
Roucis

(10) Patent No.: US 7,849,754 B2
(45) Date of Patent: Dec. 14, 2010

(54) METHOD AND SYSTEM FOR SAMPLING SYNGAS

(75) Inventor: John B. Roucis, Richmond, CA (US)

(73) Assignee: General Electric Company, Schenectady, NY (US)

( * ) Notice: Subject to any disclaimer, the term of this patent is extended or adjusted under 35 U.S.C. 154(b) by 488 days.

(21) Appl. No.: 11/964,100

(22) Filed: Dec. 26, 2007

(65) Prior Publication Data

US 2009/0165575 A1 Jul. 2, 2009

(51) Int. Cl.
 *G01N 1/22* (2006.01)
(52) U.S. Cl. .................................................. 73/863.11
(58) Field of Classification Search ....................... None
 See application file for complete search history.

(56) References Cited

U.S. PATENT DOCUMENTS

| | | | | |
|---|---|---|---|---|
| 3,468,104 A | * | 9/1969 | Willett | 96/361 |
| 3,938,390 A | * | 2/1976 | Grey | 73/863.11 |
| 4,393,703 A | * | 7/1983 | Schneider | 73/866.5 |
| 4,781,358 A | * | 11/1988 | Langan | 266/80 |
| 5,109,708 A | * | 5/1992 | Lawless | 73/863.11 |
| 5,596,155 A | | 1/1997 | Holland | |
| 5,777,241 A | * | 7/1998 | Evenson | 73/863.11 |
| 6,148,678 A | * | 11/2000 | Chapman | 73/863.11 |
| 6,701,794 B2 | | 3/2004 | Mayeaux | |
| 6,739,178 B2 | | 5/2004 | Dimarzo et al. | |
| 6,782,767 B2 | | 8/2004 | Amory et al. | |
| 6,812,710 B2 | | 11/2004 | Weyl et al. | |
| 6,883,363 B2 | | 4/2005 | Weyl et al. | |
| 7,004,041 B2 | | 2/2006 | Mayeaux | |
| 7,183,115 B1 | | 2/2007 | Lauglin | |
| 2007/0068809 A1 | | 3/2007 | Bruck et al. | |
| 2007/0147467 A1 | | 6/2007 | Arnold et al. | |
| 2008/0202261 A1 | * | 8/2008 | Felix et al. | 73/863.23 |

* cited by examiner

*Primary Examiner*—Robert R Raevis
(74) *Attorney, Agent, or Firm*—Armstrong Teasdale LLP

(57) ABSTRACT

A method is provided for sampling hot gas. The method includes inserting a probe into a flow of hot gas, and collecting a sample of the hot gas with the probe. The sample of the hot gas is quenched prior to an analysis of the sample.

20 Claims, 3 Drawing Sheets

US 7,849,754 B2

METHOD AND SYSTEM FOR SAMPLING SYNGAS

BACKGROUND OF THE INVENTION

The field of the present invention relates generally to combined-cycle power systems, and more specifically, to methods and systems for use in sampling raw and/or purified syngas in a combined-cycle power system.

At least some known combined cycle power systems used for power generation include a gasification system that is integrated with at least one power-producing turbine system. For example, known gasifiers convert a mixture of fuel, air or oxygen, steam, and/or limestone into an output of partially combusted gas, sometimes referred to as "raw syngas," or syngas, generally. Combustion gases are supplied from the combustor to a gas turbine engine, which powers a generator that supplies electrical power to a power grid. Exhaust from at least some known gas turbine engines is supplied to a heat recovery steam generator that generates steam for driving a steam turbine. Power generated by the steam turbine also drives an electrical generator that provides additional electrical power to the power grid.

Generally, a process environment of the gasifier, radiant syngas cooler (RSC), and/or other gasification-related equipment, is required to be sampled to enable a base case analysis, and to enable advanced computational methods to be applied for improving gasifier designs. Currently, an apparatus for collecting reliable in situ basic data within the RSC and/or other related equipment is not available. Rather, only thermocouples have been applied at various locations to obtain data within the harsh reaction environment. Unfortunately, because of high temperatures and/or gas phase solids present in the process environment, the results of such approaches are generally limited and may not be reliable.

BRIEF DESCRIPTION OF THE INVENTION

In one aspect, a method is provided for sampling hot gas. The method includes inserting a probe into a flow of hot gas, and collecting a sample of the hot gas with the probe. The sample of the hot gas is quenched prior to an analysis of the sample.

In another aspect, a system is provided for sampling hot gas. The system includes a probe configured to be inserted into a flow of hot gas for collecting a sample of the hot gas. The system also includes a fluid source configured to channel cooling fluid for quenching the sample prior to an analysis of the sample.

In yet another aspect, a probe configured to be inserted into a flow of hot syngas through a gasifier to facilitate sampling the hot syngas is provided. The probe includes a body including a collection channel extending axially through the body and configured to collect a sample of the syngas. The probe also includes a cooling channel positioned radially outward from the collection channel and configured to channel cooling fluid to quench the sample prior to an analysis of the sample.

DETAILED DESCRIPTION OF THE INVENTION

As used herein, the term "syngas," refers to the products of gasification reactions including the full spectrum of gasification products related to, for example, coal gasification. Such products include, but are not limited to, slag, metals, unconverted carbon species, and other chemical species associated with gasification.

The present invention provides a probe that may be inserted into a flow of hot syngas through a radiant syngas cooler to facilitate sampling the hot syngas. More specifically, the probe collects gas phase reactants and reaction products, as well as solids associated with the gasification process. The reaction samples are rapidly quenched with nitrogen to facilitate reducing reaction rates, and to facilitate minimizing particulate agglomeration, such that the reaction sample can be accurately analyzed. Specifically, gas composition, temperature, gas particulate morphology, gas path concentration, particle heat transfer properties of the gas, and radiative syngas properties of the syngas can be analyzed using the present invention, while retaining the chemical and physical characteristics of the raw syngas stream in a state similar to that realized within the raw syngas stream within the process equipment being sampled. The probe can also be moved radially within the reaction environment to provide samples for analysis of radial dependence.

It should be noted that although the present invention is described with respect to a combined-cycle power system, one of ordinary skill in the art should understand that the present invention is not limited to being used only in a combined-cycle power system. Rather, the present invention may be used in any system having a fluid flowing therethrough that requires sampling. Further, for simplicity, the present invention is described herein only with respect to inserting a probe into the flow of syngas through a radiant syngas cooler. However, as would be appreciated by one of ordinary skill in the art, the present invention is not limited to inserting a probe into a radiant syngas cooler; but rather, the probe may be used to sample any hot gas from any source.

Figure 1:
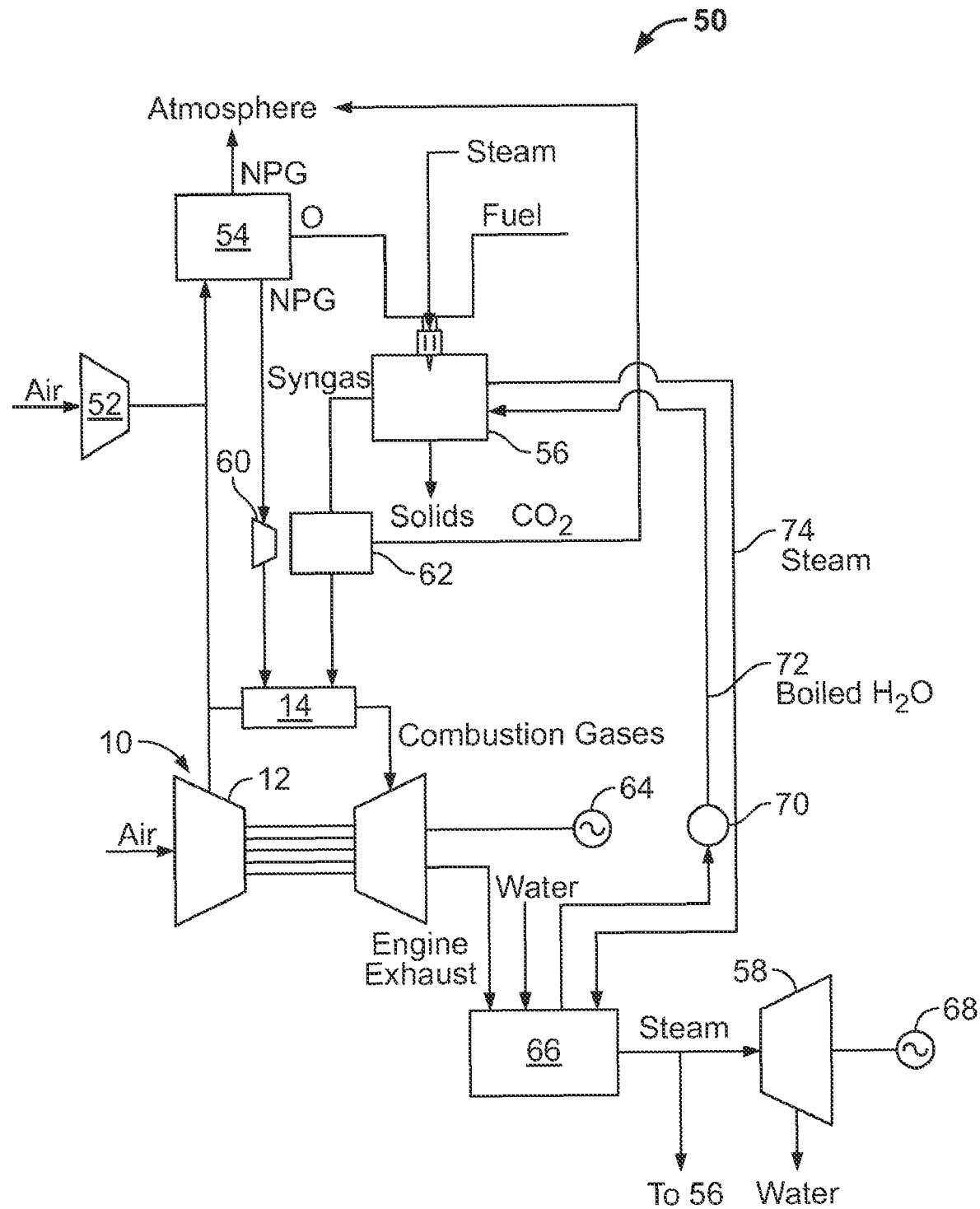
FIG. 1 is a schematic diagram of an exemplary combined cycle power system.

FIG. 1 is a schematic diagram of an exemplary combined-cycle power system 50. In the exemplary embodiment, system 50 includes a main air compressor 52, an air separation unit 54 coupled in flow communication to compressor 52, a gasifier 56 coupled in flow communication to air separation unit 54, a gas turbine engine 10, coupled in flow communication to gasifier 56, and a steam turbine 58.

In operation, compressor 52 compresses ambient air that is channeled to air separation unit 54. In some embodiments, in addition to compressor 52 or alternatively to, compressed air from gas turbine engine compressor 12 is supplied to air separation unit 54. Air separation unit 54 uses the compressed air to generate oxygen for use by gasifier 56. More specifically, air separation unit 54 separates the compressed air into separate flows of oxygen ($O_2$) and a gas by-product, sometimes referred to as a "process gas". The process gas generated by air separation unit 54 includes nitrogen and will be referred to herein as "nitrogen process gas" (NPG). The NPG may also include other gases such as, but not limited to, oxygen and/or argon. For example, in some embodiments, the NPG includes between about 95% and about 100% nitrogen. The $O_2$ flow is channeled to gasifier 56 for use in generating partially combusted gases, referred to herein as "syngas" for use by gas turbine engine 10 as fuel, as described below in more detail. In some known systems 50, at least some of the NPG flow is vented to the atmosphere from air separation unit 54. Moreover, in some known systems 50, some of the NPG flow is injected into a combustion zone (not shown) within gas turbine engine combustor 14 to facilitate controlling emissions of engine 10, and more specifically to facilitate reducing the combustion temperature and nitrous oxide emissions generated within engine 10. In the exemplary embodiment, system 50 includes a compressor 60 for compressing the nitrogen process gas flow before being injected into the combustion zone.

Gasifier 56 converts a mixture of fuel, $O_2$ supplied by air separation unit 54, steam, and/or limestone into an output of syngas for use by gas turbine engine 10 as fuel. Although gasifier 56 may use any fuel, in some known systems 50, gasifier 56 uses coal, petroleum coke, residual oil, oil emulsions, tar sands, and/or other similar fuels. In some embodiments of system 50, the syngas generated by gasifier 56 includes carbon dioxide. In the exemplary embodiment, syngas generated by gasifier 52 is cleaned in a clean-up device 62 before being channeled to gas turbine engine combustor 14 for combustion thereof. Carbon dioxide ($CO_2$) may be separated from the syngas during clean-up and, in some embodiments of system 50, may be vented to the atmosphere. Gas turbine engine 10 drives a generator 64 that supplies electrical power to a power grid (not shown). Exhaust gases from gas turbine engine 10 are channeled to a heat recovery steam generator 66 that generates steam for driving steam turbine 58. Power generated by steam turbine 58 drives an electrical generator 68 that provides electrical power to the power grid. In some known systems 50, steam from heat recovery steam generator 66 is supplied to gasifier 56 for generating syngas.

Furthermore, in the exemplary embodiment, system 50 also includes a pump 70 that supplies steam 72 from steam generator 66 to a radiant syngas cooler (not shown) within gasifier 56 to facilitate cooling the syngas flowing within gasifier 56. Steam 72 is channeled through the radiant syngas cooler wherein water 72 is converted to steam 74. Steam 74 is then returned to steam generator 66 for use within gasifier 56 or steam turbine 58.

Figure 2:
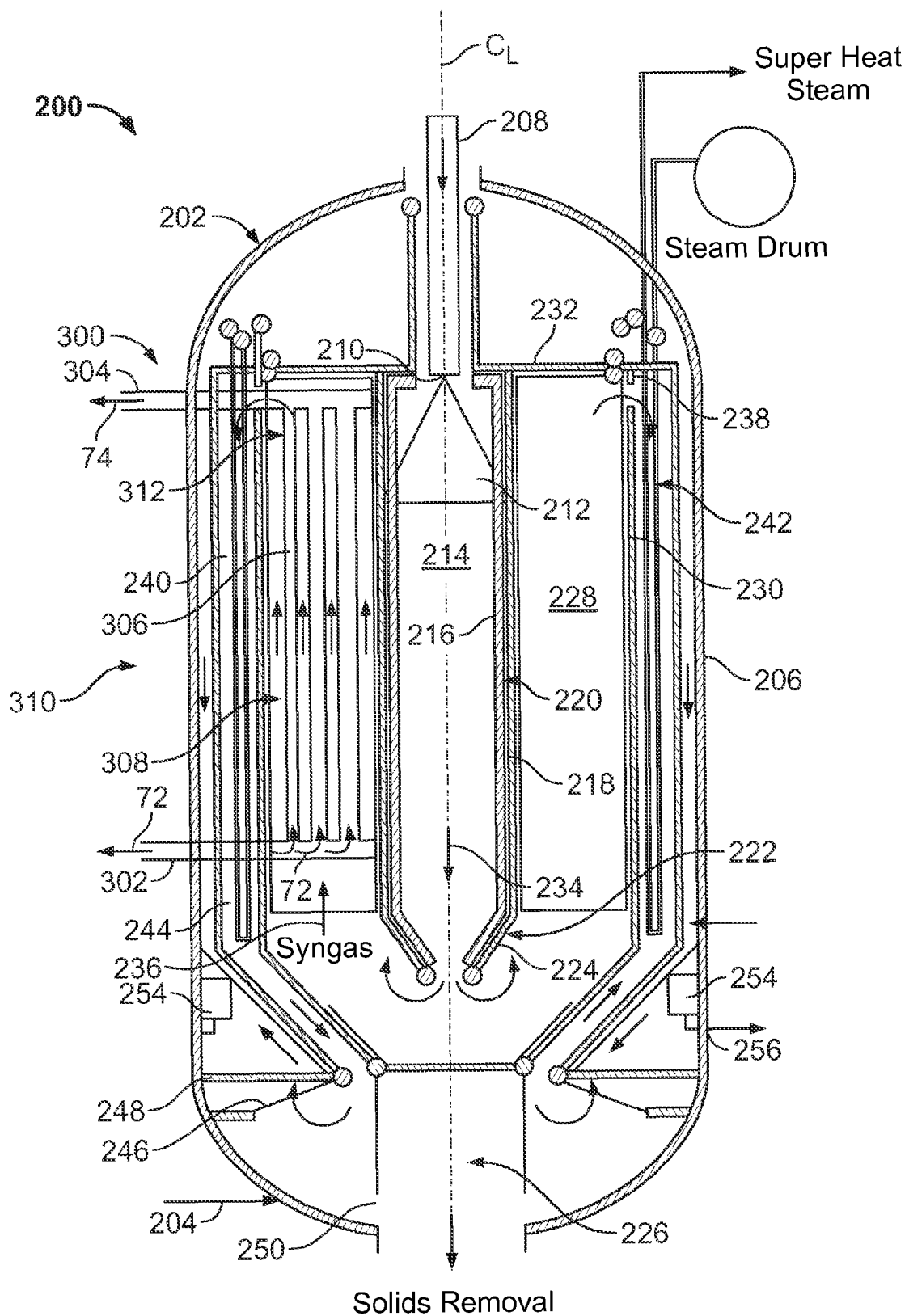
FIG. 2 is a schematic side view of an exemplary gasifier that may be used with the combined cycle power system shown in FIG. 1.

FIG. 2 is a schematic view of an exemplary advanced solids removal gasifier 200 that includes an integral radiant syngas cooler 300. Gasifier 200 may be used with a power system, such as system 50 (shown in FIG. 1). In the exemplary embodiment, gasifier 200 includes an upper shell 202, a lower shell 204, and a substantially cylindrical vessel body 206 extending therebetween. A feed injector 208 penetrates upper shell 202 to enable a flow of fuel to be channeled into gasifier 200. More specifically, fuel flowing through injector 208 is routed through one or more passages (not shown) defined in feed injector 208 and is discharged through a nozzle 210 in a predetermined pattern 212 into a combustion zone 214 defined in gasifier 200. The fuel may be mixed with other substances prior to entering nozzle 210, and/or may be mixed with other substances when discharged from nozzle 210. For example, the fuel may be mixed with fines recovered from a process of system 50 prior to entering nozzle 210 and/or the fuel may be mixed with an oxidant, such as air or oxygen, at nozzle 210, or downstream from nozzle 210.

In the exemplary embodiment, combustion zone 214 is defined as a vertically-oriented, generally cylindrical space, that is substantially co-aligned with nozzle 210 and in a serial flow communication. In the exemplary embodiment, a refractory wall 216 that includes a structural substrate 218 and a refractory coating 220 that substantially resists the effects of high temperatures and high pressures contained within combustion zone 210 defines an outer periphery of combustion zone 210. In the exemplary embodiment, an outlet end 222 of refractory wall 216 includes a convergent outlet nozzle 224 that facilitates maintaining a predetermined backpressure in combustion zone 214, while permitting products of combustion and syngas generated in combustion zone 214 to exit combustion zone 214. Such products of combustion may include, but are not limited to including, gaseous byproducts, slag formed on refractory coating 220, and/or fine particular matter carried in suspension with the gaseous byproducts.

After exiting combustion zone 214, flowable slag and solid slag are gravity-fed into a lockhopper 226 coupled to bottom shell 204. Lockhopper 226 is maintained with a level of water that facilitate quenching the flowable slag into a brittle solid material that may be broken into smaller pieces when removed from gasifier 200. In the exemplary embodiment, lockhopper 226 captures approximately ninety percent of fine particulate exiting combustion zone 214.

In the exemplary embodiment, an annular passage 228 at least partially surrounds combustion zone 214. Passage 228 is partially defined by refractory wall 216 at an inner periphery, and by a cylindrical shell 230 that is substantially coaxially aligned with combustion zone 214 at a radially outer periphery of first passage 228. First passage 228 is substantially sealed at its top by an upper flange 232. Gaseous byproducts, and any remaining fine particulate, are channeled from a downward direction 234 in combustion zone 214 to an upward direction 236 in passage 228. The rapid redirection at outlet nozzle 224 facilitates separating fine particulate and slag separation from gaseous byproducts.

Gaseous byproducts and any remaining fine particulate are channeled upward through passage 228 to an outlet 238. As the gaseous byproducts are channeled through passage 228, heat may be recovered from the gaseous byproducts and the fine particulate. For example, in one embodiment, the gaseous byproducts enter passage 228 at a temperature of approximately 2500° Fahrenheit and exit passage 228 at a temperature of approximately 1800° Fahrenheit. The gaseous byproducts and fine particulates are discharged from passage 228 through outlet 238 and are channeled into a second annular passage 240 wherein the gaseous byproducts and fine particulates are redirected to a downward flow direction 241. As gaseous byproducts and fine particulates flow through passage 240, heat may be recovered using, for example, superheat tubes 242 that transfer heat from the flow of gaseous byproducts and the fine particulates to steam flowing through superheat tubes 242. For example, in one embodiment, the gaseous byproducts enter passage 240 at a temperature of approximately 1800° Fahrenheit and exit passage 240 at a temperature of approximately 1500° Fahrenheit.

When the flow of gaseous byproducts and the fine particulates reach a bottom end 244 of passage 240, passage 240 converges toward lockhopper 226. More specifically, at passage bottom end 244, the flow of gaseous byproducts and the fine particulates is channeled upward through a water spray 246 that facilitates desuperheating the flow of gaseous byproducts and the fine particulates. Heat removed from the flow of gaseous byproducts and the fine particulates facilitates vaporizing water spray 246 and agglomerating the fine particulates, such that the fine particulates form a relatively larger ash conglomerate that falls into lower shell 204. The flow of gaseous byproducts and the remaining fine particulates are then channeled in a reverse direction towards a perforated plate 248 that circumscribes bottom end 244. A level of water is maintained above perforated plate 248 to facilitate removing additional fine particulate from the flow of gaseous byproducts. As the flow of gaseous byproducts and the remaining fine particulates are percolated through perforated plate 248, fine particulates contained in the flow are entrapped in the water and carried through the perforations into a sump formed in bottom shell 204. A gap 250 defined between lockhopper 226 and bottom shell 204 enables the fine particulates to flow into lockhopper 226 wherein the fine particulates are facilitated to be removed from gasifier 200.

An entrainment separator 254 encircles an upper end of lower shell 204. More specifically, in the exemplary embodiment, separator 254 is above perforated plate 248 and above the level of water covering perforated plate 248. Entrainment separator 254 may be for example, a cyclonic or centrifugal separator that includes a tangential inlet or turning vanes that impart a swirling motion to the gaseous byproducts and the remaining fine particulates flowing therethrough. The particulates are thrown outward by centrifugal force to the walls of separator 254 wherein the fine particulates coalesce and are gravity-fed to the separator bottom shell 204. Additionally, any remaining fine particulates impact a mesh pad, agglomerate with other particulates, and are flushed to bottom shell 204.

Alternatively, entrainment separator 254 may be a blade type separator, such as a chevron separator or an impingement separator. In a chevron separator, the gaseous byproducts pass between blades and are forced to travel in a tortuous path. The entrained particulates, and any liquid droplets, cannot follow the gas streamlines, and are impinged against the blade surfaces prior to coalescing, wherein the particulates are gravity-fed into bottom shell 204. Features such as hooks and pockets, can be added to the sides of the blades to facilitate improving particulate and liquid droplet capture. In addition, chevron grids can be stacked to provide a series of separation stages. Similarly, impingement separators create a cyclonic motion as gaseous byproducts and fine particulates pass over contoured blades. A spinning motion is imparted that causes the entrained particulates and any liquid droplets to be forced against the vessel walls, wherein the entrained particulates and any liquid droplets may be collected in bottom shell 204.

The flow of gaseous byproducts and any remaining fine particulates enter separator 254 wherein substantially all of any remaining entrained particulate and/or liquid droplets are removed form the flow of gaseous byproducts. The flow of gaseous byproducts exits gasifier 200 through an outlet 256 for further processing.

In the exemplary embodiment, gasifier 200 also includes a radiant syngas cooler 300 that is coupled within passage 228. In the exemplary embodiment, cooler 300 includes an inlet 302, an outlet 304, and a plurality of cooling tubes 306 that extend between inlet 302 and outlet 304. Each cooling tube 306 is positioned within passage 228 to facilitate cooling syngas flowing through passage 228.

In the exemplary embodiment, inlet 302 extends from a first end 308 of each cooling tube 306 to an exterior 310 of cylindrical vessel 206. Similarly, outlet 304 extends from a second end 312 of each cooling tube 306 to exterior 310. In the exemplary embodiment, inlet 302 is positioned below outlet 304. In an alternative embodiment, inlet 302 is positioned above outlet 304 or is substantially co-planar therewith.

During operation, pump 70 channels steam 72 from steam generator 66 through inlet 302 and into cooling tube first end 308. Alternatively, steam 72 may be channeled to inlet 302 from any suitable source. Steam 72 is then channeled through cooling tube 306 towards second end 312. Simultaneously, syngas channeled through passage 228 flows around cooling tube 306 to facilitate heat transfer between the syngas and steam 72. Specifically, because steam 72 has a temperature that is less than the temperature of the syngas, steam 72 absorbs heat from the syngas to facilitate cooling the syngas.

Furthermore, in addition to cooling the syngas, each cooling tube 306 facilitates the cooling of refractory wall 216. More specifically, as steam 72 absorbs heat from the syngas, a higher temperature steam 74 is produced in each cooling tube 306. In the exemplary embodiment, steam 74, at the higher temperature, is discharged from outlet 304 to steam generator 66 for further use within system 50. In an alternative embodiment, steam 74 is channeled to any suitable portion of system 50 and/or any other system that requires steam. In another alternative embodiment, steam 74 is discharged from system 50 to the atmosphere.

Figure 3:
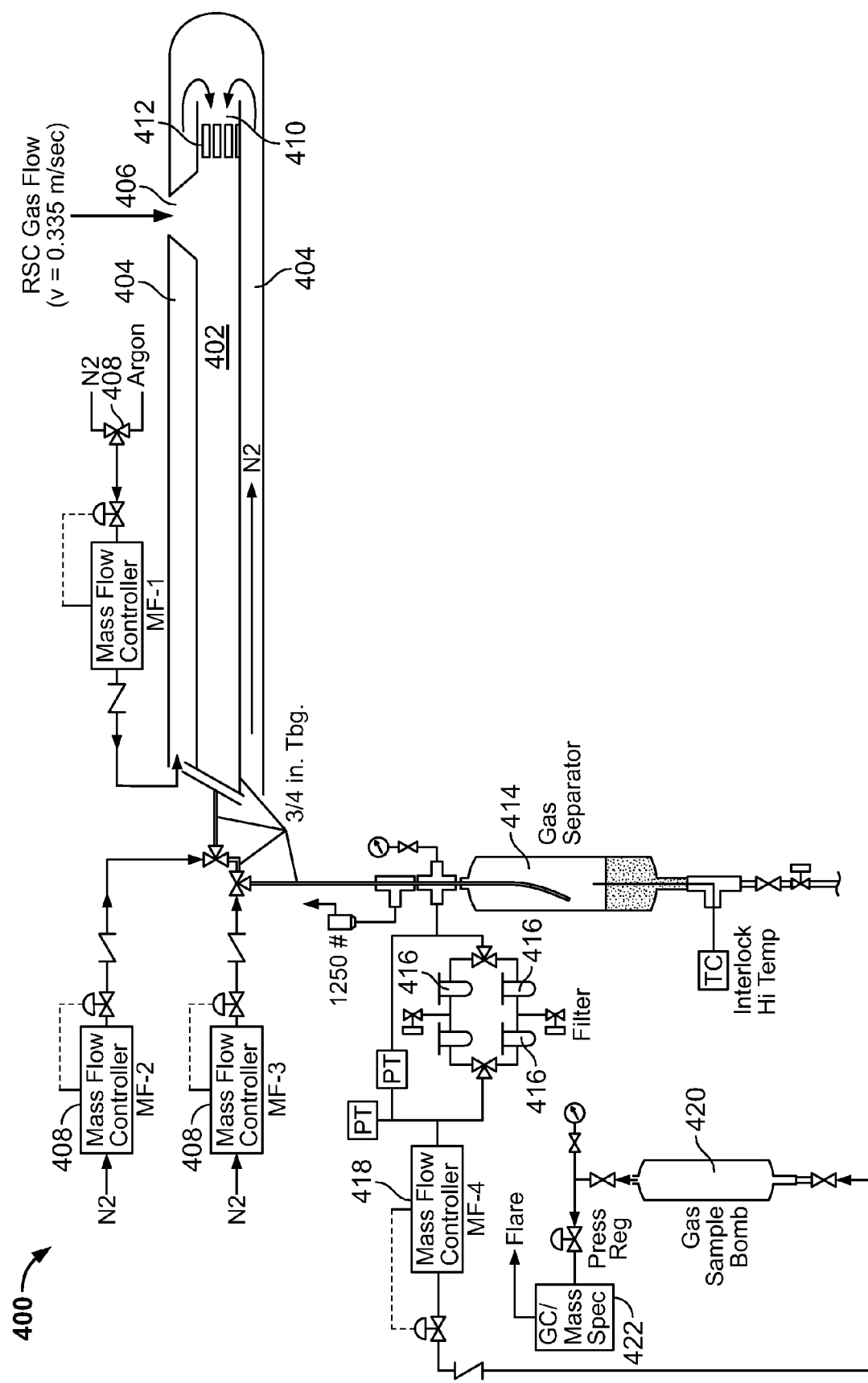
FIG. 3 is a schematic view of a probe that may be used to sample syngas and/or solid gasification products contained within a syngas stream flowing through a portion of the gasifier shown in FIG. 2.

FIG. 3 is a schematic view of a probe 400 that may be used to sample syngas and/or solid gasification products contained within a syngas stream flowing through radiant syngas cooler 300 (shown in FIG. 2). Probe 400 includes a collection channel 402 and a cooling channel 404 that is positioned adjacent to, and in flow communication with, collection channel 402. Collection channel 402 collects a sample of the syngas from radiant syngas cooler 300. Specifically, probe 400 is inserted into radiant syngas cooler 300 and into the flow of syngas such that a sample of the syngas is channeled through an opening 406 defined in probe 400 and into collection channel 402. In the exemplary embodiment, probe 400 is moved radially within radiant syngas cooler 300 to provide syngas samples for analysis of radial dependence within radiant syngas cooler 300. In an alternative embodiment, probe 400 is inserted into radiant syngas cooler 300 at any suitable angle that enables probe 400 to function as described herein. Although the exemplary embodiment is described with respect to inserting probe 400 into radiant syngas cooler 300, as will be appreciated by one of ordinary skill in the art, probe 400 may be inserted into any portion of gasifier 200 and/or combined-cycle power system 50. Further, although probe 400 is described with respect to collecting a sample of syngas, as will be appreciated by one of ordinary skill in the art, probe 400 may be used to collect a sample of any fluid.

In the exemplary embodiment, cooling channel 404 channels a cooling fluid from at least one cooling fluid source 408 to facilitate cooling and quenching the sample of syngas to enable analysis of the sample. In the exemplary embodiment, the cooling fluid is nitrogen gas. However, as will be appreciated by one of ordinary skill in the art, in an alternative embodiment, the cooling fluid may be any suitable fluid that facilitates quenching the syngas sample as is described herein, such as, but not limited to, an inert gas, for example, argon. In the exemplary embodiment, heat transfer between collection channel 402 and cooling channel 404 facilitates cooling of the syngas. Further, the cooling fluid is channeled through an opening 410 defined in collection channel 402 and is mixed with the syngas sample in the collection channel 402 to facilitate quenching the syngas. In the exemplary embodiment, the cooling fluid is channeled through a plurality of injection channels 412 that provide cooling fluid stream lines as the cooling fluid quenches the syngas. In an alternative embodiment, the cooling fluid is channeled into collection channel 402 through any suitable structure that enables probe 400 to function as described herein. In the exemplary embodiment, the syngas sample is rapidly quenched by reducing the temperature of the sample through dilution of the sample, with the cooling fluid, to facilitate reducing reaction rates and to minimize particulate agglomeration.

In the exemplary embodiment, the quenched syngas is channeled to a gas separator 414 wherein particulate matter within the syngas sample is separated from the sample. In the exemplary embodiment, the syngas sample is collected through probe 400 until gas separator 414 is filled with particulate matter, other solids, and/or condensed liquid reaction products. In an alternative embodiment, the syngas sample is collected until a predetermined amount of syngas needed for testing has been collected. In the exemplary embodiment, the particulate matter collected in gas separator 414 is analyzed to collect analytical data on the syngas sample and/or particulate matter. For example, the particulate matter is analyzed to determine data, such as, but not limited to, particle morphology, particle concentration, particle heat transfer properties, particle volume fraction, particle size distribution, particle composition, and other unspecified analytical methods applied to the particulate and/or gaseous matter collected.

The remaining syngas is channeled from gas separator 414 and is either filtered by a plurality of filters 416 and/or bypasses filters 416. A mass flow controller 418 channels the syngas through a gas sample bomb 420 and through an analysis device 422 and/or devices connected in series or parallel to sample the flow path. In one embodiment, analysis device 422 is a GC/mass spectrometer. Alternatively, as will be appreciated by one of ordinary skill in the art, the analysis device 422 may be any device capable of analyzing syngas, as described herein. In the exemplary embodiment, analysis device 422 enables analysis of the quenched syngas sample under inert conditions. In the exemplary embodiment, the syngas is analyzed for at least one of, but not limited to, chemical composition, gas emissivity, absorption coefficients, and/or radiative heat flux to syngas cooler platens and/or walls.

In one embodiment, a method is provided for sampling hot gas. The method includes inserting a probe into a flow of hot gas, and collecting a sample of the hot gas with the probe. The sample of the hot gas is quenched prior to an analysis of the sample. In the exemplary embodiment, the probe is inserted into a flow of hot syngas through a radiant syngas cooler. Further, in the exemplary embodiment, the sample is quenched with nitrogen.

In one embodiment, the quenched sample is analyzed with a GC/mass spectrometer. In another embodiment, the quenched sample is analyzed under inert conditions. Further, in one embodiment, the method also includes collecting particles and/or condensable species from the quenched sample. Moreover, in one embodiment, the method also includes filtering the quenched sample.

The above-described systems and methods facilitate acquiring syngas data that is currently unavailable using known syngas testing. More specifically, the above-described systems and methods enable the collection of hot syngas samples flowing through a radiant syngas stream that contains particles and condensables. Through quenching, the hot syngas can be analyzed under inert conditions. Accordingly, the syngas can be tested more efficiently and reliably. As such, operation of the radiant syngas cooler and/or the combined cycle power system can be improved, thereby increasing the efficiency of the radiant syngas cooler and/or the combined cycle power system while reducing costs associated with operating and maintaining the radiant syngas cooler and/or the combined cycle power system.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Exemplary embodiments of systems and methods for sampling syngas are described above in detail. The systems and methods illustrated are not limited to the specific embodiments described herein, but rather, components of the system may be utilized independently and separately from other components described herein. Further, steps described in the method may be utilized independently and separately from other steps described herein.

While the invention has been described in terms of various specific embodiments, those skilled in the art will recognize that the invention can be practiced with modification within the spirit and scope of the claims.

What is claimed is:

1. A method for sampling hot gas, said method comprising:
   inserting a probe into a flow of hot gas, wherein the probe includes a plurality of injection channels, the probe further includes a collection channel positioned downstream from the plurality of injection channels and a cooling channel positioned adjacent to and in flow communication with the collection channel;
   collecting a sample of the hot gas with the probe; and
   quenching the sample of the hot gas prior to an analysis of the sample.

2. A method in accordance with claim 1, further comprising separating particles from the quenched sample.

3. A method in accordance with claim 1, further comprising analyzing the quenched sample under inert conditions.

4. A method in accordance with claim 1, wherein said quenching the sample further comprises quenching the sample with a flow of nitrogen.

5. A method in accordance with claim 1, further comprising analyzing the quenched sample using a spectrometer.

6. A method in accordance with claim 1, further comprising filtering the quenched sample.

7. A method in accordance with claim 1, inserting a probe into a flow of hot gas further comprises inserting a probe into a flow of hot syngas channeled through a gasifier.

8. A system for sampling hot gas, said system comprising:
   a probe configured to be inserted into a flow of hot gas for collecting a sample of the hot gas, wherein said probe includes a plurality of injection channels, said probe further includes a collection channel positioned downstream from said plurality of injection channels and a cooling channel positioned adjacent to and in flow communication with said collection channel; and
   a fluid source configured to channel cooling fluid for quenching the sample prior to an analysis of the sample.

9. A system in accordance with claim 8, further comprising a gas separator configured to separate particles from the quenched sample.

10. A system in accordance with claim 8, wherein the cooling fluid comprises nitrogen.

11. A system in accordance with claim 8, further comprising a spectrometer used to analyze the quenched sample.

12. A system in accordance with claim 11, wherein the spectrometer analyzes the sample under inert conditions.

13. A system in accordance with claim 8, further comprising at least one filter used to filter the quenched sample.

14. A system in accordance with claim 8, wherein said probe is configured to analyze at least one of a gas emissivity and an absorption coefficient of the hot gas.

15. A probe configured to be inserted into a flow of hot syngas through a gasifier to facilitate sampling the hot syngas, said probe comprising a body comprising:
   a plurality of injection channels;
   a collection channel positioned downstream from said plurality of injection channels, said collection channel extending axially through the body and configured to collect a sample of the syngas; and a cooling channel positioned radially outward from the collection channel and configured to channel cooling fluid to quench the sample prior to an analysis of the sample.

16. A probe in accordance with claim 15, wherein said probe is configured to channel the quenched sample to a gas separator that separates particles from the quenched sample.

17. A probe in accordance with claim 15, wherein said probe facilitates analyzing the quenched sample under inert conditions.

18. A probe in accordance with claim 15, wherein the cooling fluid comprises nitrogen.

19. A probe in accordance with claim 15, wherein said probe is configured to channel the quenched sample to a spectrometer used to analyze the quenched sample.

20. A probe in accordance with claim 15, wherein said probe is configured to channel the quenched sample to at least one filter used to filter the quenched sample.

* * * * *